(12) United States Patent
Jochemsen et al.

(10) Patent No.: US 11,419,792 B2
(45) Date of Patent: Aug. 23, 2022

(54) MEDICINE DISPENSING DEVICE AND METHOD FOR DISPENSING MEDICINE

(71) Applicant: VMI HOLLAND B.V., Epe (NL)

(72) Inventors: Kees Jochemsen, Epe (NL); Ton De Boer, Epe (NL)

(73) Assignee: VMI HOLLAND B.V.

( * ) Notice: Subject to any disclaimer, the term of this patent is extended or adjusted under 35 U.S.C. 154(b) by 0 days.

(21) Appl. No.: 17/282,966

(22) PCT Filed: Sep. 27, 2019

(86) PCT No.: PCT/NL2019/050651
§ 371 (c)(1),
(2) Date: Apr. 5, 2021

(87) PCT Pub. No.: WO2020/071905
PCT Pub. Date: Apr. 9, 2020

(65) Prior Publication Data
US 2021/0386628 A1 Dec. 16, 2021

(30) Foreign Application Priority Data

Oct. 5, 2018 (NL) ..................................... 2021768

(51) Int. Cl.
*A61J 7/00* (2006.01)
*G16H 20/13* (2018.01)
(Continued)

(52) U.S. Cl.
CPC ........... *A61J 7/0084* (2013.01); *A61J 7/0069* (2013.01); *A61J 7/02* (2013.01); *G07F 11/18* (2013.01); *G16H 20/13* (2018.01)

(58) Field of Classification Search
CPC ............ A61J 7/02; A61J 7/0069; B65B 5/103
See application file for complete search history.

(56) References Cited

U.S. PATENT DOCUMENTS

| 4,101,284 A | * | 7/1978 | Difiglio ............ G01N 33/54366 221/95 |
| 4,693,057 A | | 9/1987 | Rittinger et al. ....... B65B 35/30 |

(Continued)

FOREIGN PATENT DOCUMENTS

| CN | 105705043 | 6/2016 | ............. B65B 35/12 |
| CN | 207580205 | 7/2018 | ............... B65B 1/30 |

(Continued)

OTHER PUBLICATIONS

Netherlands Search Report issued in Netherlands Patent Appln. Serial No. 2021768, dated Jun. 21, 2019, 8 pages.

(Continued)

*Primary Examiner* — Timothy R Waggoner
(74) *Attorney, Agent, or Firm* — Hayes Soloway P.C.

(57) ABSTRACT

Disclosed is a medicine dispensing device and a method for dispensing medicine, wherein the medicine dispensing device includes a tray and a drop plate below the tray in a drop direction, wherein the drop plate is slidable relative to the tray between a hold position and a drop position, wherein the medicine dispensing device further includes one or more retaining members for retaining the drop plate relative to the tray in the drop direction when the drop plate is in a dispensing path, wherein the drop plate is slidable in a release direction into a release position outside of the dispensing path, wherein the one or more retaining members are arranged for releasing the drop plate from the tray in the release position.

37 Claims, 7 Drawing Sheets

(51) Int. Cl.
*G07F 11/18* (2006.01)
*A61J 7/02* (2006.01)

(56) References Cited

U.S. PATENT DOCUMENTS

| | | | | |
|---|---|---|---|---|
| 4,771,912 | A * | 9/1988 | van Wingerden | A01C 7/02 221/75 |
| 5,291,191 | A | 3/1994 | Moore | 340/825.35 |
| 2004/0074916 | A1 | 4/2004 | Priebe et al. | 221/289 |
| 2009/0260330 | A1* | 10/2009 | Hess | B65B 35/06 53/235 |
| 2014/0261883 | A1* | 9/2014 | Dent | G16H 20/13 141/192 |
| 2016/0151244 | A1* | 6/2016 | Hellenbrand | A61J 1/16 206/438 |
| 2016/0302468 | A1 | 10/2016 | Robinson | A23P 1/142 |

FOREIGN PATENT DOCUMENTS

| | | | | |
|---|---|---|---|---|
| DE | 2853768 | 7/1980 | | B65B 1/00 |
| EP | 2 110 324 | 10/2009 | | B65B 35/06 |
| JP | 3123201 | 6/2006 | | A61J 7/00 |

OTHER PUBLICATIONS

International Preliminary Report on Patentability issued in PCT/NL2019/050651, dated Oct. 1, 2020, 8 pages.
International Search Report and Written Opinion issued in PCT/NL2019/050651, dated Mar. 4, 2020, 9 pages.
Chinese Official Action issued in Chinese Patent Appln. Serial No. 2019800652932, dated May 27, 2022, 10 pages.

\* cited by examiner

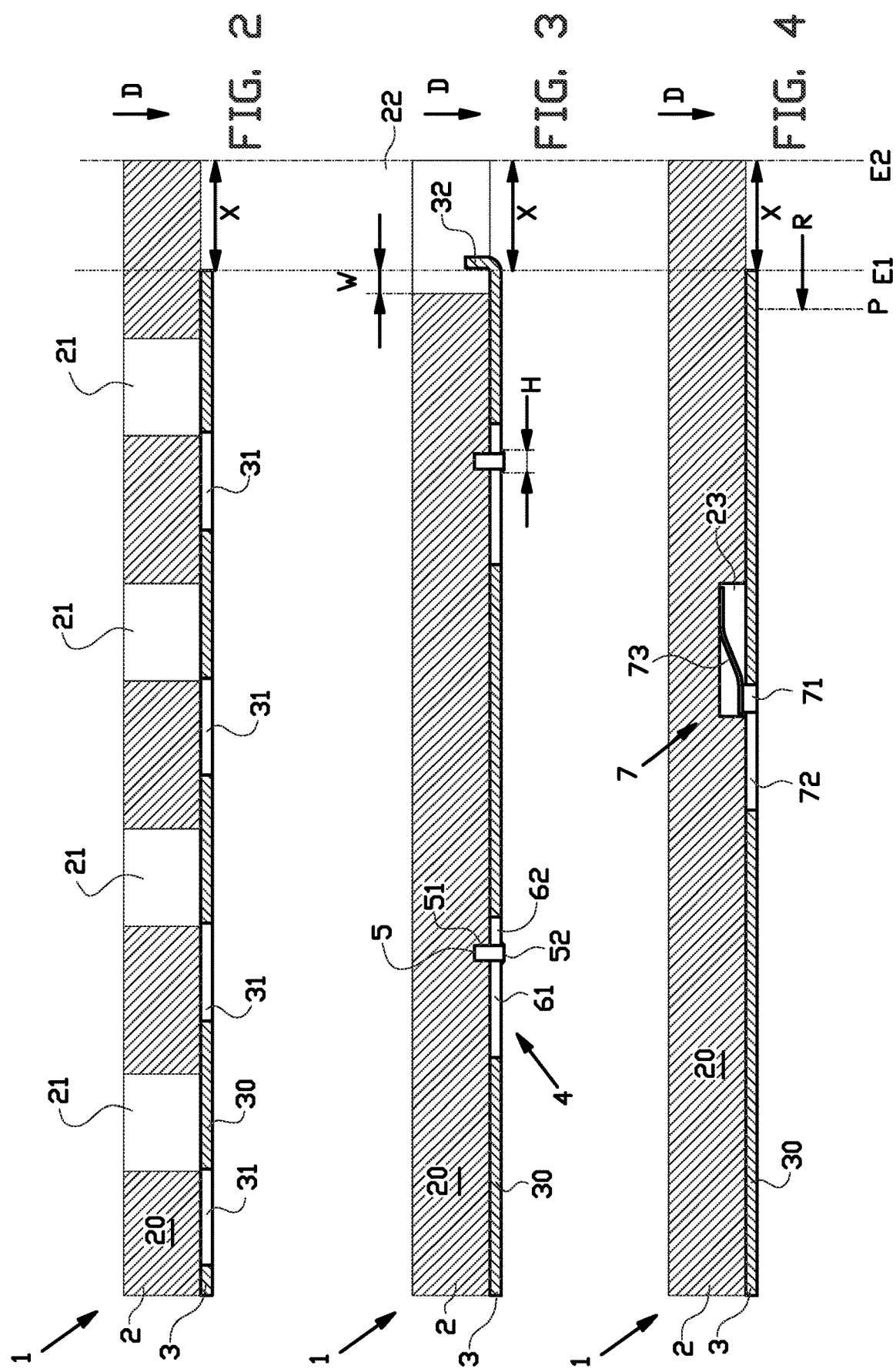

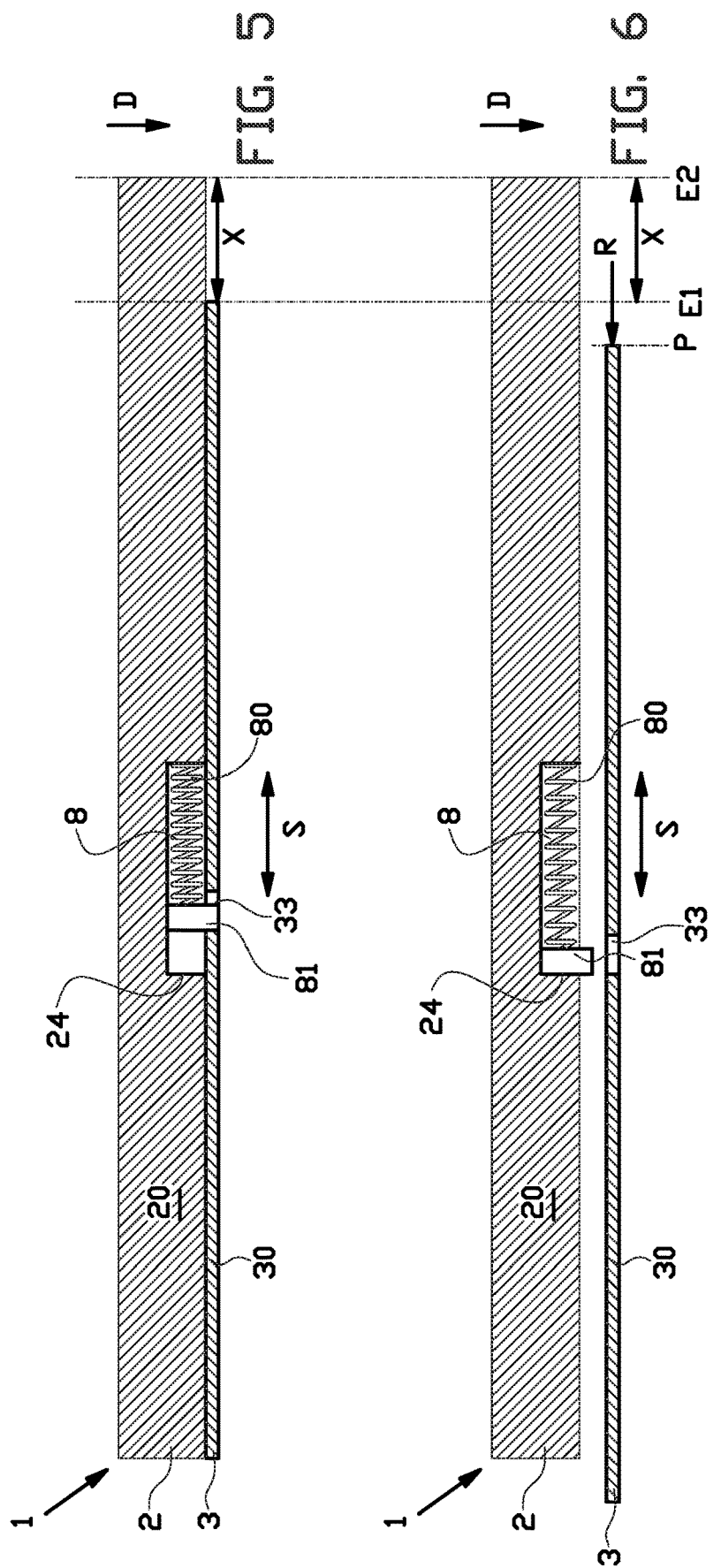

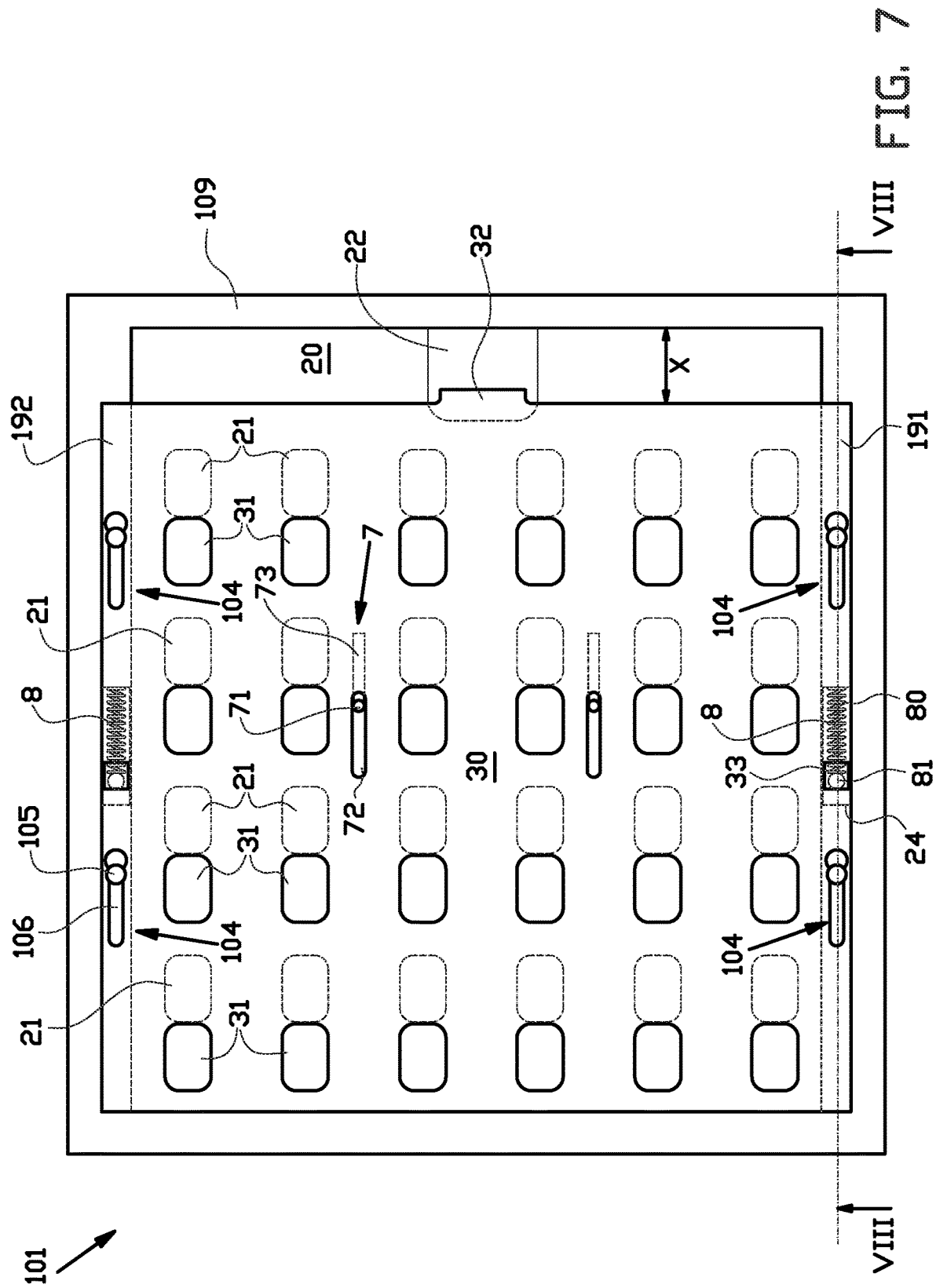

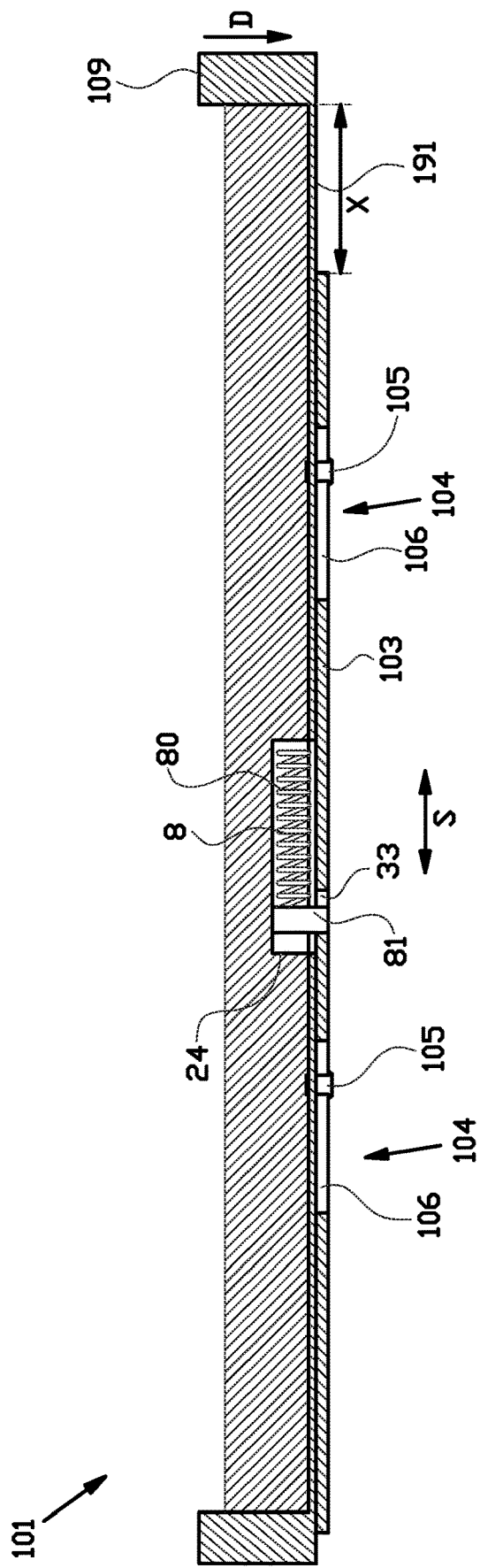

MEDICINE DISPENSING DEVICE AND METHOD FOR DISPENSING MEDICINE

BACKGROUND

The invention relates to a medicine dispensing device and a method for dispensing medicine.

US 2004/074916 A1 discloses a pill counter with a removable sizing guide provided with apertures and a movable plate with similar apertures as the sizing guides. The housing side walls can have grooves, rails, channels, ridges or any other type of recesses or protrusions to support the movable plate relative to the sizing guides. The movable plate is slidable with respect to the sizing guides between two positions. After the movable plate is inserted into the housing, a plate lock is inserted into a slot in the housing such that its main body extends downwards past the plate, thereby preventing the plate from being easily removed or falling out of the housing when the pill counter is shaken. When the plate lock is removed the movable plate can be released from the housing in a sliding direction parallel to the grooves in the housing side walls by sliding the movable plate completely clear of the housing in said sliding direction.

US 2016/151244 A1 discloses a device for feeding individual portions of drugs. The device includes a transporting tray with a plurality of upwardly open accommodating compartments which are arranged in a single plane and are intended for accommodating one or more individual portions of drugs. The device also includes a carrying frame accommodating the tray. The carrying frame includes a closing plate that is movable relative to the tray into a drug transfer position to free the individual portions of drugs from the accommodating compartments. The tray is arranged in a removable manner in the carrying frame to provide simple access to the closing plate so that it is easy to clean. To further simplify cleaning of the closing plate, in one preferred embodiment they may be detachably attached to the device to allow thorough cleaning or disinfecting of the closing plate at regular intervals.

SUMMARY OF THE INVENTION

A disadvantage of the pill counter disclosed in US 2004/074916 A1 is that the grooves in the housing side walls are likely to collect dust and other pollutants while they are relatively inaccessible and therefore hard to clean. Although the device disclosed in US 2016/151244 A1 does not have that problem, it has the disadvantage that the closing plate is attached to the device with a considerable number of retaining means. At each cleaning interval, an operator has to individually loosen and remove each of the retaining means. This is a laborious task, in particular when the cleaning interval is relatively short.

It is an object of the present invention to provide a medicine dispensing device and a method for dispensing medicine, wherein the medicine dispensing device can be kept clean more easily.

According to a first aspect, the invention provides a medicine dispensing device comprising a tray and a drop plate below the tray in a drop direction, wherein the tray is provided with a plurality of storage cavities for receiving one or more medicine items, wherein the drop plate is slidable relative to the tray in a sliding direction perpendicular to the drop direction between a hold position and a drop position, wherein the drop plate is provided with a plurality of drop openings which are out of line with the plurality of storage cavities in the drop direction when the drop plate is in the hold position and which are aligned with the plurality of storage cavities in the drop direction when the drop plate is in the drop position, wherein the medicine dispensing device further comprises one or more retaining members for retaining the drop plate relative to the tray in the drop direction when the drop plate is in a dispensing path extending from a first endpoint defined by one of the hold position and the drop position up to a second endpoint defined by the other one of the drop position and the hold position, wherein the drop plate is slidable in a release direction into a release position outside of the dispensing path, wherein the one or more retaining members are arranged for releasing the drop plate in the drop direction from the tray in said release position.

The sliding of the drop plate into the release position is an act that can be performed relatively easily either as an extension of the sliding that already occurs within the dispensing path or in a release direction transverse to said sliding direction. There is no need to loosen and remove each retaining member individually. The sliding of the drop plate into the release position can be effectuated in the same way as the sliding of the drop plate within the dispensing path, i.e. preferably manually without the need to use tools. By taking the drop plate and the tray apart in the drop direction, any mechanical interlock for facilitating the sliding relationship between the tray and the drop plate can be quickly and/or effectively terminated, i.e. without the need for relatively long guides, slots or grooves in the sliding direction. Once the drop plate is released from the tray, the drop plate and/or the tray can be cleaned. The drop plate and the tray can be put back together again in the reverse order with the same ease, i.e. by positioning the drop plate in the release position relative to the tray and by subsequently sliding the drop plate in the sliding direction from the release position into any position within the dispensing path.

In one embodiment, the drop plate at least partially overlaps with the tray in the release direction when the drop plate is in the release position. This allows for the drop plate to be released from the tray without sliding the drop plate completely clear of the tray in the release direction.

Preferably, the release direction is parallel to the sliding direction. The movement of the drop plate into the release position can thus be a continuation of the sliding movement of the drop plate in the dispensing path.

More preferably, the release position is located outside of the dispensing path beyond the first endpoint.

Alternatively, the release direction is transverse or perpendicular to the sliding direction. The release of the drop plate from the tray thus merely requires a change in the direction of movement of the drop plate from the sliding direction into the release direction.

Preferably, the release position is located outside of the dispensing path alongside said dispensing path in the release direction. The tray can thus be moved transversely out of said dispensing path at any position between the first endpoint and the second endpoint.

In a further embodiment each retaining member comprises a male element and a female element, wherein the male element is arranged to mechanically interlock with the female element to facilitate a sliding relationship between the tray and the drop plate when the drop plate is in the dispensing path, wherein the male element is arranged to terminate the mechanical interlock with the female element in the drop direction when the drop plate is in the release position. The male element can therefore automatically be disengaged from the female element in the release position, to allow for the release of the drop plate from the tray.

In an alternative embodiment each retaining member comprises a male element associated with one of the tray and the drop plate and a female element formed in the other of the tray and the drop plate, wherein the male element is arranged to engage the female element when the drop plate is in the dispensing path and wherein the male element is arranged to disengage from the female element when the drop plate is in the release position. The male element can therefore automatically be disengaged from the female element in the release position, to allow for the release of the drop plate from the tray.

Preferably, the female element comprises a retaining slot extending parallel to the sliding direction and a keyhole in communication with the retaining slot, wherein the male element comprises a stem that fits through the retaining slot in the drop direction and a head at one end of the stem that fits through the female element only at the keyhole. The head can prevent that the male element is disengaged from the female element along the retaining slot thereof while the stem facilitates the sliding of the male element through the retaining slot. The male element can therefore be in a form-locking engagement with the female element. The form-lock can however be automatically terminated as soon as the head is aligned with the keyhole.

More preferably, the retaining slot defines the dispensing path and the keyhole defines the release position. In other words, the dispensing path extends along at least a part of the retaining slot and the keyhole defines the position in which the male element, and thus the drop plate, can be released from the tray.

In a further embodiment the male element is associated with the tray and the female element is formed in the drop plate. The drop plate can therefore be kept clear of male elements protruding from its surface. As a consequence, the drop plate can be cleaned more easily and/or effectively.

In another embodiment the head has a head dimension in the sliding direction, wherein the release position is spaced apart from the first endpoint of the dispensing path in the sliding direction over a distance equal to at least half of the head dimension. Said spacing can prevent that the drop plate is unintentionally moved into the release position when accidentally moving the drop plate only slightly beyond the first endpoint.

In another embodiment the medicine dispensing device further comprises one or more blocking members for blocking and unblocking the drop plate from sliding in the release direction outside of the dispensing path towards the release position. The one or more blocking members can thus effectively prevent accidental release of the drop plate from the tray.

Preferably, each blocking member comprises a stop element associated with one of the tray and the drop plate and a catch formed in or by the other of the tray and the drop plate, wherein the stop element is arranged to abut the catch in the release direction. The abutment can effectively prevent further movement of the drop plate beyond the first endpoint.

More preferably, the catch is a catch slot extending in the sliding direction. The catch slot allows for the stop element to slide with or relative to the drop plate in the sliding direction while the boundaries of the catch slot provide the abutment when the drop plate is in the first endpoint.

In a further embodiment the stop element is associated with the tray and the catch is formed in or by the drop plate. The drop plate can therefore be kept clear of the stop element protruding from its surface. As a consequence, the drop plate can be cleaned more easily and/or effectively.

In a further embodiment the stop element is movable between a block position in which the stop element engages with the catch and an unblock position in which the stop element is disengaged from the catch, wherein each blocking member further comprises a block bias element for biasing the stop element from the unblock position into the block position. The stop element can thus be moved automatically into its block position when the drop plate is in the dispensing path.

Preferably, the stop element is manually movable against the bias of the block bias element from the block position into the unblock position. Thus, the unblocking does not require tools.

In a further embodiment the stop element and the block bias element are integrally formed. Preferably, the block bias element is a leaf spring. By having a single part, the blocking member can be simplified.

In another embodiment the medicine dispensing device further comprises one or more slide biasing members for biasing the drop plate from the drop position into the hold position. Preferably, each slide biasing member comprises a spring that acts on one or both of the tray and the drop plate in the sliding direction. Hence, the drop plate has to be actively slid into the drop position and can be automatically returned to the hold position.

In another embodiment each slide biasing member further comprises a pin that is arranged to engage the drop plate, wherein the drop plate is provided with a corresponding pin aperture for receiving said pin in the drop direction, wherein the pin aperture is positioned in the drop plate such that the pin is automatically aligned with the pin aperture in the drop direction when the drop plate is placed in the release position relative to the tray. The pin can thus be automatically coupled to the drop plate when the drop plate is in the release position, to subsequently tension the spring when the drop plate moves into the dispensing path.

In one embodiment of the invention the one or more retaining members are arranged for retaining the drop plate directly to the tray in the drop direction. By retaining the drop plate directly to the tray, no additional means are required to position the drop plate relative to the tray. In particular, no frame is required to facilitate the sliding of the drop plate relative to the frame. Hence, the medicine dispensing device can be simplified and/or has less parts that require cleaning.

In an alternative embodiment of the invention the medicine dispensing device further comprises a frame for holding the tray, wherein the one or more retaining members are arranged for retaining the drop plate directly to the frame. By having the frame, the operator can selectively remove one of the tray and the drop plate for cleaning, while the other of the tray and the drop plate can still be held at or retained to the frame.

In said alternative embodiment, it is preferred that each retaining member comprises a male element associated with one of the frame and the drop plate and a female element formed in the other of the frame and the drop plate, wherein the male element is arranged to engage the female element when the drop plate is in the dispensing path and wherein the male element is arranged to disengage from the female element when the drop plate is in the release position. The male element can therefore automatically be disengaged from the female element in the release position, to allow for the release of the drop plate from the tray.

In another embodiment the first endpoint is defined by the hold position. The release position is thus located outside of the dispensing path at the side that is defined by the hold position of the drop plate. This is particularly convenient when the drop plate is biased to return to this hold position and even more convenient when the drop plate is blocked in this hold position. The bias can then be used to bias the drop plate into the release position as soon as the drop plate has been unblocked.

According to a second aspect, the invention provides a method for dispensing medicine items using the medicine dispensing device according to any one of the aforementioned embodiments, wherein the method comprises the steps of sliding the drop plate in the release direction into the release position outside of the dispensing path and releasing the drop plate in the drop direction from the tray in said release position.

An important aspect of dispensing medicines is that the medicine dispensing device, in particular the drop plate, is cleaned regularly. As mentioned before, the medicine dispensing device according to the first aspect of the invention has technical advantages that make this cleaning relatively easy. The method relates to the practical implementation of the medicine dispensing device and thus has the same technical advantages, which will not be repeated hereafter.

Preferably, the release direction is parallel to the sliding direction. More preferably, the release position is located outside of the dispensing path beyond the first endpoint.

Alternatively, the release direction is transverse or perpendicular to the sliding direction. Preferably, the release position is located outside of the dispensing path alongside said dispensing path in the release direction.

In another preferred embodiment the drop plate is released from the tray in the drop direction.

In another embodiment the medicine dispensing device further comprises one or more blocking members for blocking and unblocking the drop plate from sliding in the release direction outside of the dispensing path towards the release position, wherein the method further comprises the step of unblocking the drop plate prior to sliding the drop plate from the dispensing path into the release position. Preferably, the drop plate is manually unblocked.

In one embodiment of the invention the drop plate is retained directly to the tray in the drop direction.

In an alternative embodiment of the invention the medicine dispensing device further comprises a frame for holding the tray, wherein the drop plate is retained directly to the frame.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an exemplary embodiment shown in the attached schematic drawings, in which:

FIGS. 2, 3, 4 and 5 show cross section views of the medicine dispensing device according to lines III-III, IV-IV and V-V, respectively, in FIG. 1;

FIG. 6 shows a cross section view according to FIG. 5 with the drop plate released from the tray;

FIG. 7 shows a bottom view of an alternative medicine dispensing device according to a second embodiment of the invention;

FIG. 8 shows a cross section view of the alternative medicine dispensing device according to line VIII-VIII in FIG. 7;

DETAILED DESCRIPTION OF THE INVENTION

FIGS. 1-6 show a medicine dispensing device 1 according to a first exemplary embodiment of the invention. The medicine dispensing device 1 is used to dispense sorted drugs, medicaments or medicine items (not shown), such as tablets or pills, or other dosed portions of medicine in a drop direction D into a collection unit of a medicine packaging machine as disclosed in WO 2014/081286 A1.

Figure 1:
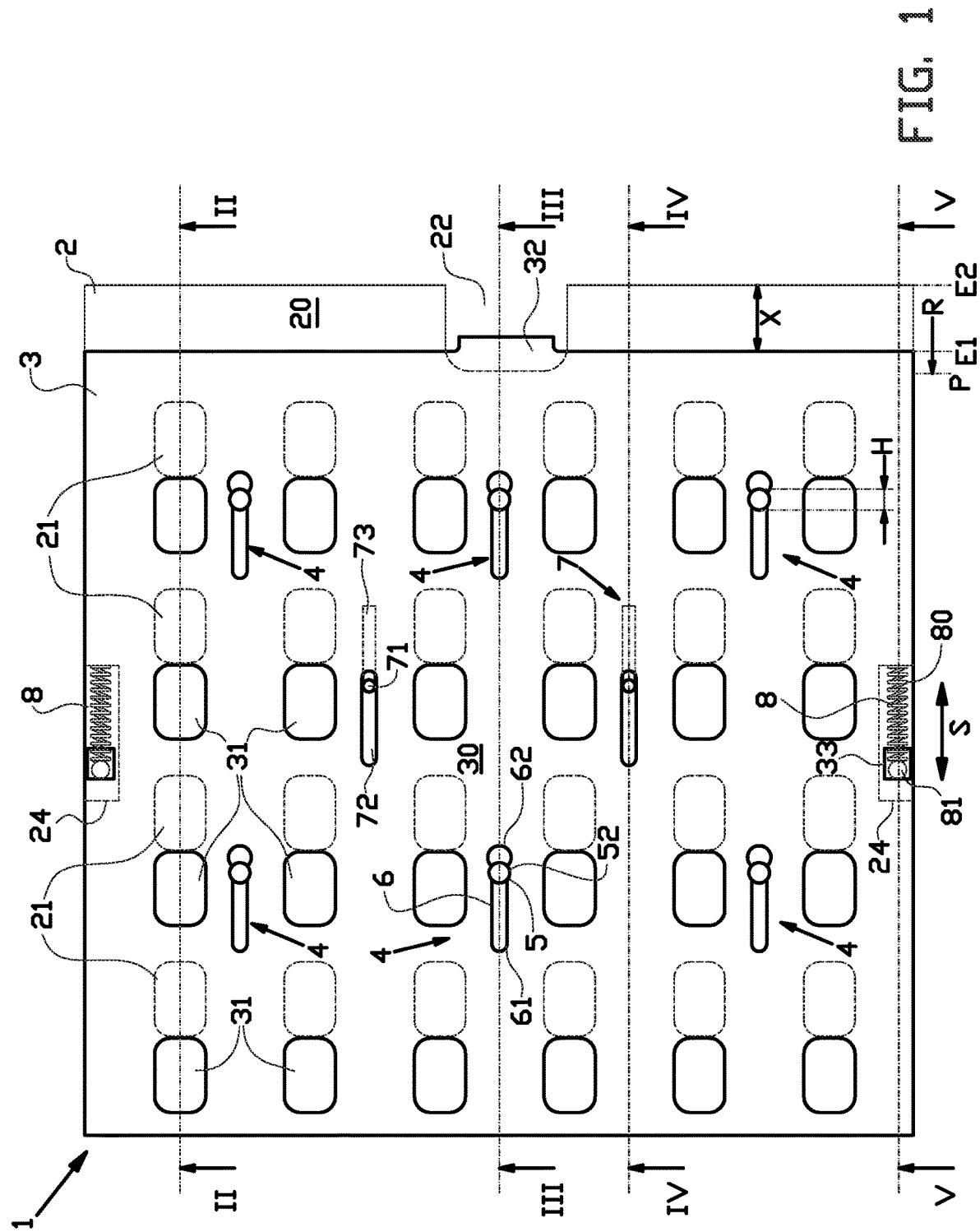
FIG. 1 shows a bottom view of a medicine dispensing device according to a first embodiment of the invention.

As best seen in FIG. 2, the medicine dispensing device 1 comprises a tray 2 and a drop plate 3 below the tray 2 in the drop direction D. The tray 2 is provided with a tray body 20 and a plurality of storage cavities 21 formed in said tray body 20 for receiving one or more of the medicine items. As shown in FIG. 1, the storage cavities 21 are arranged in an matrix of rows and columns. Alternative configurations of the storage cavities 21 also fall within the scope of this invention.

As best seen in FIG. 1, the drop plate 3 is provided with a plate body 30 and a plurality of drop openings 31 formed in said plate body 30. The drop openings 31 are dimensioned to allow for passage of the medicine items through the drop plate 3 in the drop direction D. The drop plate 3 is slidable relative to the tray 2 in a sliding direction S perpendicular to the drop direction D between a hold position, as shown in FIGS. 1-5, and a drop position. When sliding from the hold position into the drop position and vice versa, the drop plate 3 is moved relative to the tray 2 in or along a dispensing stroke or path X extending from a first endpoint E1 defined by one of the hold position and the drop position up to a second endpoint E2 defined by the other one of the drop position and the hold position. In this exemplary embodiment, the first endpoint E1 corresponds to the hold position and the second endpoint E2 corresponds to the drop position.

In the hold position, the plurality of drop openings 31 are out of line with the plurality of storage cavities 21 in the drop direction D. In other words, in the hold position, the plate body 30 effectively closes the cavities 21 in the drop direction D. In the drop position, the plurality of drop openings 31 are aligned with the plurality of storage cavities 21 in the drop direction D to drop or dispense the medicine items from the cavities 21 in said drop direction D.

In this exemplary embodiment, the number of drop openings 31 is equal to the number of cavities 21 in the tray 2. Hence, each drop opening 31 is associated with or dedicated for opening and closing a respective one of the cavities 21. More in particular, the drop openings 31 are arranged in a similar array of rows and columns, such that they are all equally offset and aligned in the hold position and the drop position, respectively. Alternatively, two or more cavities 21 may have a common drop opening, i.e. in the form of a drop slot 13 not shown but known per se—that can be aligned with several cavities 21 at once.

As best seen in FIG. 3, the drop plate 3 is provided with a pull member 32 to manually pull the drop plate 3 in the sliding direction S from the hold position at the first endpoint E1 into the drop position at the second end point E2. As shown in FIGS. 1 and 3, the tray body 20 is provided with a corresponding pull recess 22 at the location of said pull member 32 to allow manual access to said pull member 32. Note that the pull member 32 is spaced apart from the tray body 20 in the hold position at the first endpoint E1 over a clearance W, as shown in FIG. 3, that allows for further sliding movement of the drop plate 3 beyond the first endpoint E1, as will be explained in more detail hereafter.

The drop direction D is preferably vertical or substantially vertical, so that the medicine items may drop from the cavities 21 under the influence of gravity.

In the exemplary embodiment as shown in FIG. 2, the cavities 21 are open at the side of the tray body 20 that faces away from the drop plate 3, i.e. the upper side of the tray body 20, to receive the medicine items from above. In an alternative embodiment—not shown—the cavities 21 may be closed at the side of the tray body 20 that faces away from the drop plate 3, in which case medicine dispensing device 1 can be inverted to receive the medicine items via the drop openings 31 of the drop plate 3 into the cavities 21. The drop plate 3 is then moved into the hold position to close the cavities 21 and the medicine dispensing device 1 is turned back to its original orientation. From that moment, the medicine dispensing device 1 can dispense the medicine items from the cavities 21 through the drop openings 31 in the same way as previously described.

As shown in FIGS. 1 and 3, the medicine dispensing device 1 further comprises one or more retaining members 4 for retaining the drop plate 3 relative to the tray 2 in the drop direction D when the drop plate 3 is in the dispensing path X between the first endpoint E1 and the second endpoint E2. In this exemplary embodiment, the one or more retaining members 4 are arranged for coupling, connecting and/or retaining the drop plate 3 directly to the tray 2, i.e. without additional means such as a frame. Preferably, the one or more retaining members 4 are located in a central area of the tray 2 and/or the drop plate 3, i.e. spaced apart from the edges thereof, to prevent deflection of said drop plate 3 relative to the tray 2, in particular when said drop plate 3 is relative large and thin.

As best seen in FIG. 1, each retaining member 4 comprises a male element 5 associated with one of the tray 2 and the drop plate 3 and a female element 6 formed in the other of the tray 2 and the drop plate 3. Preferably, the male element 5 and the female element 6 are arranged to engage with each other through some form of mechanical interlock, i.e. a form-lock.

In particular, the female element 6 comprises a retaining slot 61 extending parallel to the sliding direction S and a keyhole 62 that is arranged in communication with said retaining slot 61 at one end of the retaining slot 61 for receiving the male element 5 from the retaining slot 61. The dispensing path X extends along or is defined by at least a part of the retaining slot 61. The dispensing path X may however be shorter than the length of the retaining slot 61, i.e. when it is limited in movement relative to the tray 2 by suitable limiting elements (not shown). As shown in FIG. 3, the male element 5 comprises a stem 51 that fits through the retaining slot 61 in the drop direction D and a head 52 at one end of the stem 51 that fits through the female element 6 only at the keyhole 62. Consequently, the keyhole 62 corresponds to or defines the release position P.

Preferably, the head 52 has a head dimension H in the sliding direction S and the release position P is spaced apart from the dispensing path X over a distance that is equal to or greater than half the head dimension H, to prevent accidental and/or unintentional release of the drop plate 3 from the tray 2. More preferably, the release position P is spaced apart from the first endpoint E1 of the dispensing path X in the sliding direction S over at least three millimeters, and preferably at least five millimeters.

In this exemplary embodiment, the female element 6 is formed in the drop plate 3 and the male element 5 is connected to, coupled with or associated with the tray 2.

The male element 5, when engaged with the female element 6, is arranged to remain engaged with the female element 6 as long as the drop plate 3 is in the dispensing path X. However, as briefly discussed before, the drop plate 3 further slidable in a release direction R outside of the dispensing path X, in particular beyond the first endpoint E1, and more in particular parallel to the sliding direction S within the clearance W as shown in FIG. 3. As such, the drop plate 3 may be slid into a release position P in which one or more retaining elements 4 are arranged to release the drop plate 3 from the tray 2 in the drop direction D. In particular, the male element 5 is arranged to disengage from the female element 6 when the drop plate 3 is in the release position P. More in particular, the release position P corresponds to the position in which the head 52 of the male element 5 is aligned with the keyhole 62 of the female element 6.

It is noted that the drop plate 3 still at least partially overlaps with the tray 2 in the release direction R when the drop plate 3 is in the release position P, as for example shown in FIG. 6. This allows for the drop plate 3 to be released from the tray 2 without sliding the drop plate 3 completely clear of the tray 2 in the release direction R. In other words, the drop plate 3 only has to be moved over a small distance beyond the dispensing path X to be released from the tray 2.

The one or more retaining members 4 are arranged for releasing the drop plate 3 from the tray 2 in the drop direction D so that the mechanical interlock between the male element 5 and female element 6 can be terminated quickly and effectively. More specifically, the head 52 of the male element 5 can be retracted through the keyhole 62 of the female element 6 in a direction parallel to the drop direction D to release the drop plate 3 from the tray 2.

In addition or as an alternative to said spacing, the medicine dispensing device 1 is provided with one or more blocking members 7, as shown in FIGS. 1 and 4, for blocking and unblocking the drop plate 3 from sliding in the release direction R outside of the dispensing path X, in particular beyond the first endpoint E1 of the dispensing path X, towards and/or into the release position P. Preferably, each blocking member 7 comprises a stop element 71 associated with one of the tray 2 and the drop plate 3 and a catch 72 formed in or by the other of the tray 2 and the drop plate 3. In this exemplary embodiment, the stop element 71 is associated with, connected to or formed by the tray 2 and the catch 72 is associated with, formed in or formed by the drop plate 3. The stop element 71 is arranged to abut the catch 72 in the release direction R when the drop plate 3 is in the first endpoint E1 of the dispensing path X.

The stop element 71 is movable between a block position in which the stop element 71 engages with the catch 72 and an unblock position in which the stop element 71 is disengaged from the catch 72. Preferably, each blocking member 7 further comprises a block bias element 73 for biasing the stop element 71 from the unblock position into the block position. More preferably, the stop element 71 is manually movable, i.e. without tools, against the bias of the block bias element 73 from the block position into the unblock position.

The catch 72 may be conveniently shaped as a catch slot that extends in the sliding direction S. The catch slot can be positioned in such a way that it receives or accommodates the stop element 71 when the drop plate 3 is at any position along the dispensing path X. In particular, the stop element 71 is biased to automatically move into a block position in the catch slot as soon as the drop plate 3 is in the dispensing path X.

As best seen in FIG. 4, the stop element 71 and the block bias element 72 are integrally formed. In this exemplary embodiment, the block bias element 72 is a leaf spring that is directly connected to or integral with the stop element 71.

In this exemplary embodiment, the tray 2 is provided with one or more blocking member accommodation recesses 23 for accommodating at least a part of a respective one of the one or more blocking members 7, in particular the block bias element 72 thereof.

As shown in FIGS. 1, 5 and 6, the medicine dispensing device 1 further comprises one or more slide biasing members 8 for biasing the drop plate 3 from the drop position into the hold position. Preferably, each slide biasing member 8 comprises a spring 80 that acts on one or both of the tray 2 and the drop plate 3 in the sliding direction S. In this exemplary embodiment, the tray 2 is provided with one or more slide bias slots 24 for accommodating at least a part of a respective one of the one or more slide biasing members 8. Each slide bias slot 24 extends in or parallel to the sliding direction S.

In this exemplary embodiment, each slide biasing member 8 further comprises a pin 81 that is arranged to engage the drop plate 3, as shown in FIG. 5. The drop plate 3 is provided with a corresponding pin aperture 33 that is suitable dimensioned to receive and retain said pin 81 in the drop direction D. As shown in FIG. 6, the pin aperture 33 is preferably suitable positioned in the drop plate 3 such that the pin 81 is automatically aligned with the pin aperture 33 in the drop direction D when the drop plate 3 is placed in the release position P relative to the tray 2. In particular, the corresponding slide bias slot 24 in the tray 2 is of such a length that the pin 81 stays behind in the slide bias slot 24 resting against one end of said slide bias slot 24 when the drop plate 3 is released from the tray 2, wherein said one end of the bias slot 24 corresponds to or is aligned with the pin aperture 33 in the drop direction D. Hence, no additionally actions are required to couple the slide biasing member 8 with the drop plate 3, other than just simply placing the drop plate 3 in the release position P and moving it into the dispensing path X to tension the spring 80.

The combination of the slide biasing member 8, the blocking member 7 means that after the drop plate 3 has been moved against the bias of the slide biasing member 8 into the drop position to drop the medicine items, it can be biased to automatically return to the hold position where it is blocked by the blocking member 7 against further sliding towards the release position P. Preferably, the slide biasing member 8 still biases the drop plate 3 in the hold position so that, when the drop plate 3 is unblocked, the bias from the slide biasing member 8 automatically causes the drop plate 3 to move towards and/or into the release position P.

A method for dispensing medicine items using the aforementioned medicine dispensing device 1 will be elucidated below with reference to FIGS. 1-6.

During a method of dispensing medicine, the drop plate 3 and/or the tray 2 need to be cleaned regularly, i.e. at specified intervals. The method therefore comprises the step of sliding the drop plate 3 in the release direction R into the release position P outside of the dispensing path X, in particular beyond the first endpoint E1 of the dispensing path X, and releasing the drop plate 3 from the tray 2 in said release position P. The sliding of the drop plate 3 into the release position P is an act that can be performed relatively easily as an extension of the sliding that already occurs within the dispensing path X. There is no need to loosen and remove each retaining member 7 individually. The sliding of the drop plate 3 into the release position P can be effectuated in the same way as the sliding of the drop plate 3 within the dispensing path X, i.e. preferably manually without the need to use tools. Once the drop plate 3 is released from the tray 2, the drop plate 3 and/or the tray 2 can be cleaned.

The drop plate 3 and the tray 2 can be put back together again in the reverse order with the same ease, i.e. by positioning the drop plate in the release position relative to the tray and by subsequently sliding the drop plate in the sliding direction from the release position into any position within the dispensing path.

When the drop plate 3 is blocked by the one or more blocking member 7 in the hold position, the method comprises the unblocking the drop plate 3 prior to the sliding of the drop plate 3 into the release position P. The unblocking may be performed manually. Conveniently, when the drop plate 3 is biased to move in the sliding direction S towards the release position P, then the drop plate 3 merely requires manual unblocking and the bias on the drop plate 3 will do the rest.

FIGS. 7 and 8 show an alternative medicine dispensing device 101 according to a second embodiment of the invention that differs from the previously discussed medicine dispensing device 1 in that it is provided with a frame 109 to receive and/or hold the tray 2 and in that it comprises a slightly modified drop plate 103 that is arranged to be connected, coupled and/or retained directly to the frame 109 instead of the tray 2. Hence, the drop plate 3 is still retained relative to the tray 2, yet indirectly via the frame 109.

In particular, the alternative medicine dispensing device 101 comprises one or more alternative retaining members 104 for retaining the drop plate 103 directly to the frame 109. For this purpose, the alternative retaining members 104 are moved to a position close to the frame 109 to engage said frame 109. In particular, each alternative retaining members 104 comprises a male element 105 and a female element 106 similar to the ones previously described, yet positioned close to or at the frame 109 to facilitate the direct retaining of the drop plate 103 to the frame 109. In this particular embodiment, the male element 105 is provided at the frame 109 and the female element 106 is provided at or formed in the drop plate 103.

Preferably, the frame 109 is provided with one or more flanges 191, 192 that act as a sliding guide for the sliding movement of the drop plate 103 relative to the tray 2. The one or more alternative retaining members 104 may be provided at the location of said one or more flanges 191, 192.

Figure 9:
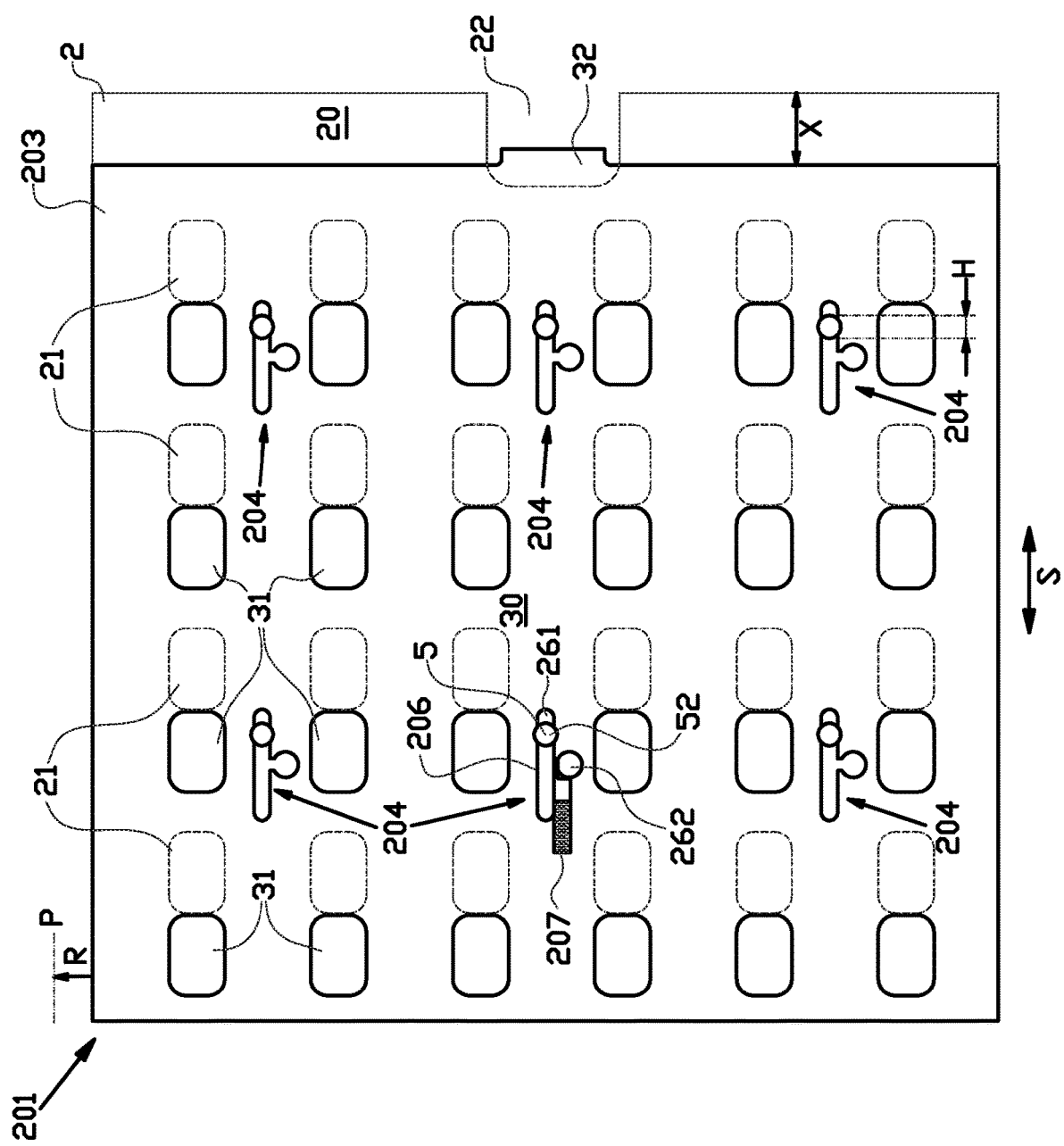
FIG. 9 shows a bottom view of a further alternative medicine dispensing device according to a third embodiment of the invention.

FIG. 9 shows a further alternative medicine dispensing device 201 according to a third embodiment of the invention that differs from the previously discussed medicine dispensing devices 1, 101 in that it features a drop plate 203 that is arranged to be moved in a release direction R that is transverse or perpendicular to said sliding direction S. Consequently, the release position P of the drop plate 203 is located outside of the dispensing path X in a direction transverse or perpendicular to said dispensing path X.

In this particular example, the further alternative medicine dispensing device 201 comprises one or more retaining members 204 that differs from the previously discussed retaining members 4, 104 in that its female element 206 is provided with a retaining slot 261 extending in the sliding direction S and a keyhole 262 to the side of the retaining slot 261 in a direction parallel to the release direction R. The keyhole 262 communicates with the retaining slot 261 to receive the male element 5 when the drop plate 203 is moved in the release direction R. In this exemplary embodiment, the keyhole 262 is located at a position alongside the retaining slot 261 somewhere along the length of the retaining slot 261, i.e. at an intermediate position between the first endpoint E1 and the second endpoint E2. Alternatively, the keyhole 262 may be arranged alongside the retaining slot 261 at or near one of the ends of the retaining slot 261.

In the further alternative dispensing device 201 according to the third embodiment of the invention, the drop plate 203 can thus be moved out of the dispensing path X when the male element 5 is aligned with the keyhole 262 in a direction parallel to the release direction R.

To prevent that the drop plate 203 is accidentally released from the tray 2 when its male element 5 is aligned with the keyhole 262, the further alternative dispensing device 201 is provided with one or more blocking members 207 that are movable into a block position for blocking the movement of the drop plate 203 in the release direction R. The one or more blocking members 207 can be manually moved into an unblock position. Preferably, the one or more blocking members 207 are biased to move into the block position. In this exemplary embodiment, at least one of the one or more blocking members 207 is movable into a block position between the retaining slot 261 and the keyhole 262 of a respective one of the retaining members 204 to block access to the keyhole 262 from the retaining slot 261. Effectively, this prevents that the drop plate 203 can be moved in the release direction R.

Optionally, the drop plate 203 may be biased to move from the drop position into the hold position, i.e. with a slide biasing member similar to the slide biasing member as previously described, provided that said slide biasing member does not interfere with the transverse movement in the release direction R. The drop plate 203 may for example be provided with a slot-shaped aperture extending in the release direction R to receive the pin of the slide biasing member. Alternatively, the slide biasing member may have an alternative rest position offset in the release direction R, yet aligned with the pin aperture when the drop plate 203 is in the release position P.

Figure 10:
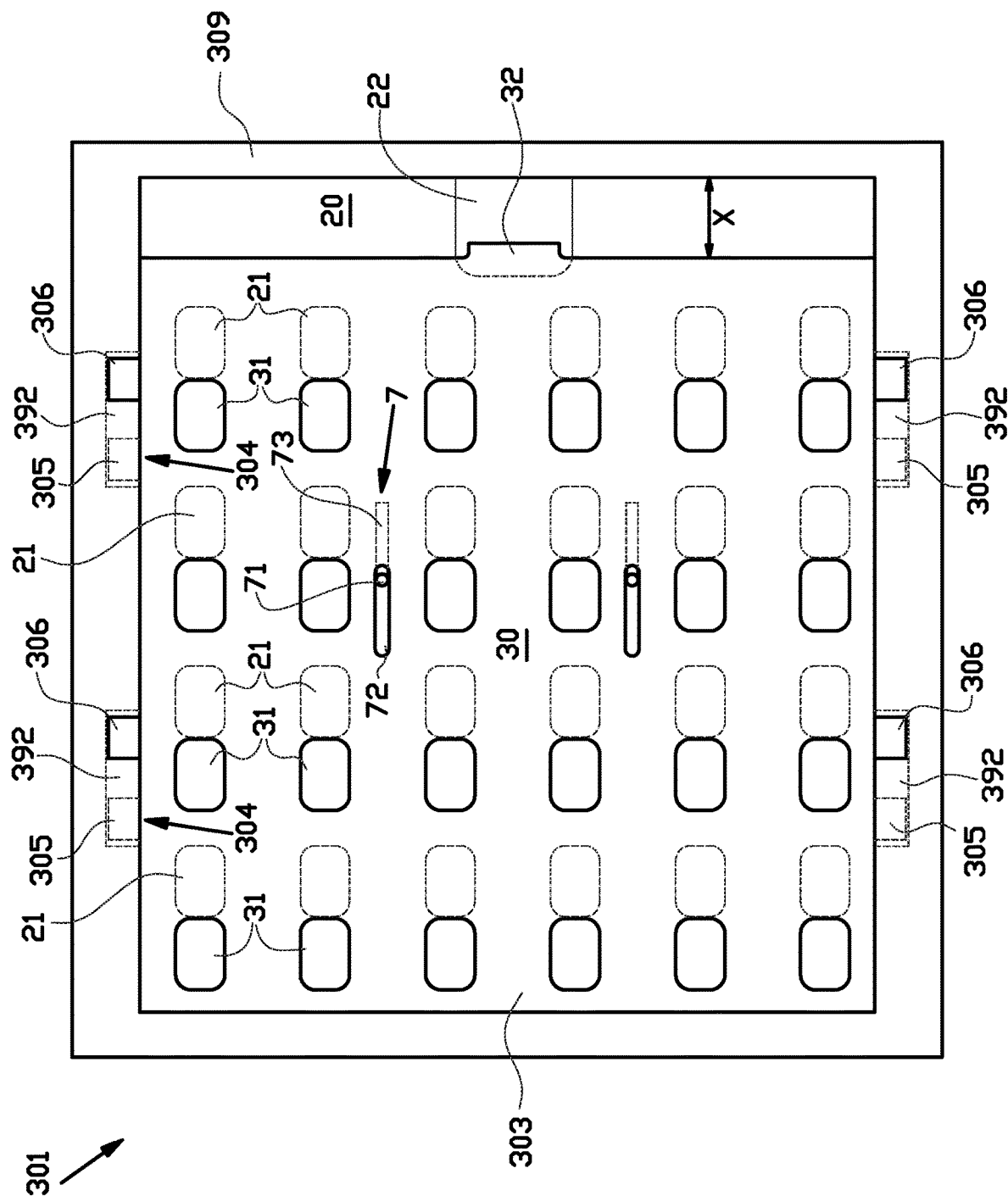
FIG. 10 shows a bottom view of a further alternative medicine dispensing device according to a fourth embodiment of the invention.

FIG. 10 shows a bottom view of a further alternative medicine dispensing device 301 according to a fourth embodiment of the invention. The further alternative medicine dispensing device 301 has a frame 309 similar to the frame 109 as shown in FIGS. 7 and 8, to receive and/or hold the tray 2 and a drop plate 303 that is arranged to be connected, coupled and/or retained directly to the frame 309 instead of the tray 2. The further alternative medicine dispensing device 301 differs from the previously discussed medicine dispensing devices 1, 101, 201 in that it features one or more alternative retaining members 304 different from the slot/keyhole interaction as described in the previous embodiments.

In particular, each alternative retaining members 304 still comprises a male element 305 and a female element 306. However, the male element 305 can be formed as a cam while the female element 306 can be formed as a recess that is aligned with the male element 305 in the drop direction D when the drop plate 303 is moved into the release position P. In this exemplary embodiment, the male element 305 is provided at the drop plate 303 and the female element 306 is a recess in the frame 309. The frame 309 may be provided with flanges or grooves 391, 392 that retain the male element 305 to the frame 309 in the drop direction D as long as the drop plate 303 is not in the release position P.

It is to be understood that the above description is included to illustrate the operation of the preferred embodiments and is not meant to limit the scope of the invention. From the above discussion, many variations will be apparent to one skilled in the art that would yet be encompassed by the scope of the present invention.

In summary, the invention relates to a medicine dispensing device 1, 101, 201 and a method for dispensing medicine, wherein the medicine dispensing device 1, 101, 201, 301 comprises a tray 2 and a drop plate 3, 103, 203, 303 below the tray 2 in a drop direction D, wherein the drop plate 3, 103, 203, 303 is slidable relative to the tray 2 between a hold position and a drop position, wherein the medicine dispensing device 1, 101, 201, 301 further comprises one or more retaining members 4, 104, 204, 304 for retaining the drop plate 3, 103, 203, 303 relative to the tray 2 in the drop direction D when the drop plate 3, 103, 203, 303 is in a dispensing path X, wherein the drop plate 3, 103, 203, 303 is slidable in a release direction R into a release position P outside of the dispensing path X, wherein the one or more retaining members 4, 104, 204, 304 are arranged for releasing the drop plate 3, 103, 203, 303 from the tray 2 in said release position P.

LIST OF REFERENCE NUMERALS 1 medicine dispensing device
2 tray
20 tray body
21 cavity
22 pull recess
23 blocking member accommodation recess
24 slide bias slot
3 drop plate
30 plate body
31 drop opening
32 pull member
33 pin aperture
4 retaining member
5 male element
51 stem
52 head
6 female element
61 retaining slot
62 keyhole
7 blocking member
71 stop element
72 catch/catch slot
73 block bias element
8 slide bias member
80 spring
81 pin
101 alternative dispensing device
103 drop plate
104 retaining member
105 male element
106 female element
109 frame 191 first flange
192 second flange
201 further alternative dispensing device
203 drop plate
204 retaining member
206 female element
261 retaining slot
262 keyhole
207 blocking member
301 alternative dispensing device
303 drop plate
304 retaining member
305 male element
306 female element
309 frame
391 first flange
392 second flange
D drop direction
E1 first endpoint
E2 second endpoint
H head dimension
P release position
R release direction
S slide direction
X dispensing stroke
W clearance

The invention claimed is:

1. A medicine dispensing device comprising a tray and a drop plate below the tray in a drop direction, wherein the tray is provided with a plurality of storage cavities for receiving one or more medicine items, wherein the drop plate is slidable relative to the tray in a sliding direction perpendicular to the drop direction between a hold position and a drop position, wherein the drop plate is provided with a plurality of drop openings which are out of line with the plurality of storage cavities in the drop direction when the drop plate is in the hold position and which are aligned with the plurality of storage cavities in the drop direction when the drop plate is in the drop position, wherein the medicine dispensing device further comprises one or more retaining members for retaining the drop plate relative to the tray in the drop direction when the drop plate is in a dispensing path extending from a first endpoint defined by one of the hold position and the drop position up to a second endpoint defined by the other one of the drop position and the hold position, wherein the drop plate is slidable in a release direction into a release position outside of the dispensing path, wherein the one or more retaining members are arranged for releasing the drop plate in the drop direction from the tray in said release position.

2. The medicine dispensing device according to claim 1, wherein the drop plate at least partially overlaps with the tray in the release direction when the drop plate is in the release position.

3. The medicine dispensing device according to claim 1, wherein the release direction is parallel to the sliding direction.

4. The medicine dispensing device according to claim 1, wherein the release position is located outside of the dispensing path beyond the first endpoint.

5. The medicine dispensing device according to claim 1, wherein the release direction is transverse or perpendicular to the sliding direction.

6. The medicine dispensing device according to claim 5, wherein the release position is located outside of the dispensing path alongside said dispensing path in the release direction.

7. The medicine dispensing device according to claim 1, wherein each retaining member comprises a male element and a female element, wherein the male element is arranged to mechanically interlock with the female element to facilitate a sliding relationship between the tray and the drop plate when the drop plate is in the dispensing path, wherein the male element is arranged to terminate the mechanical interlock with the female element in the drop direction when the drop plate is in the release position.

8. The medicine dispensing device according to claim 1, wherein each retaining member comprises a male element associated with one of the tray and the drop plate and a female element formed in the other of the tray and the drop plate, wherein the male element is arranged to engage the female element when the drop plate is in the dispensing path and wherein the male element is arranged to disengage from the female element when the drop plate is in the release position.

9. The medicine dispensing device according to claim 8, wherein the male element is associated with the tray and the female element is formed in the drop plate.

10. The medicine dispensing device according to claim 8, wherein the female element comprises a retaining slot extending parallel to the sliding direction and a keyhole in communication with the retaining slot, wherein the male element comprises a stem that fits through the retaining slot in the drop direction and a head at one end of the stem that fits through the female element only at the keyhole.

11. The medicine dispensing device according to claim 10, wherein the retaining slot defines the dispensing path and the keyhole defines the release position.

12. The medicine dispensing device according to claim 10, wherein the head has a head dimension in the sliding direction, wherein the release position is spaced apart from the first endpoint of the dispensing path in the sliding direction over a distance equal to at least half of the head dimension.

13. The medicine dispensing device according to claim 1, wherein the medicine dispensing device further comprises one or more blocking members for blocking and unblocking the drop plate from sliding in the release direction outside of the dispensing path towards the release position.

14. The medicine dispensing device according to claim 13, wherein each blocking member comprises a stop element associated with one of the tray and the drop plate and a catch formed in or by the other of the tray and the drop plate, wherein the stop element is arranged to abut the catch in the release direction.

15. The medicine dispensing device according to claim 14, wherein the catch is a catch slot extending in the sliding direction.

16. The medicine dispensing device according to claim 14, wherein the stop element is associated with the tray and the catch is formed in or by the drop plate.

17. The medicine dispensing device according to claim 14, wherein the stop element is movable between a block position in which the stop element engages with the catch and an unblock position in which the stop element is disengaged from the catch, wherein each blocking member further comprises a block bias element for biasing the stop element from the unblock position into the block position.

18. The medicine dispensing device according to claim 17, wherein the stop element is manually movable against the bias of the block bias element from the block position into the unblock position.

19. The medicine dispensing device according to claim 14, wherein the stop element and the block bias element are integrally formed.

20. The medicine dispensing device according to claim 19, wherein the block bias element is a leaf spring.

21. The medicine dispensing device according to claim 1, wherein the medicine dispensing device further comprises one or more slide biasing members for biasing the drop plate from the drop position into the hold position.

22. The medicine dispensing device according to claim 21, wherein each slide biasing member comprises a spring that acts on one or both of the tray and the drop plate in the sliding direction.

23. The medicine dispensing device according to claim 21, wherein each slide biasing member further comprises a pin that is arranged to engage the drop plate, wherein the drop plate is provided with a corresponding pin aperture for receiving said pin in the drop direction, wherein the pin aperture is positioned in the drop plate such that the pin is automatically aligned with the pin aperture in the drop direction when the drop plate is placed in the release position relative to the tray.

24. The medicine dispensing device according to claim 1, wherein the one or more retaining members are arranged for retaining the drop plate directly to the tray in the drop direction.

25. The medicine dispensing device according to claim 1, wherein the medicine dispensing device further comprises a frame for holding the tray, wherein the one or more retaining members are arranged for retaining the drop plate directly to the frame.

26. The medicine dispensing device according to claim 25, wherein each retaining member comprises a male element associated with one of the frame and the drop plate and a female element formed in the other of the frame and the drop plate, wherein the male element is arranged to engage the female element when the drop plate is in the dispensing path and wherein the male element is arranged to disengage from the female element when the drop plate is in the release position.

27. The medicine dispensing device according to claim 1, wherein the first endpoint is defined by the hold position.

28. A method for dispensing medicine items using the medicine dispensing device according to claim 1, wherein the method comprises the steps of sliding the drop plate in the release direction into the release position outside of the dispensing path and releasing the drop plate in the drop direction from the tray in said release position.

29. The method according to claim 28, wherein the release direction is parallel to the sliding direction.

30. The method according to claim 28, wherein the release position is located outside of the dispensing path beyond the first endpoint.

31. The method according to claim 30, wherein the release direction is transverse or perpendicular to the sliding direction.

32. The method according to claim 31, wherein the release position is located outside of the dispensing path alongside said dispensing path in the release direction.

33. The method according to claim 28, wherein the drop plate is released from the tray in the drop direction.

34. The method according to claim 28, wherein the medicine dispensing device further comprises one or more blocking members for blocking and unblocking the drop plate from sliding in the release direction outside of the dispensing path towards the release position, wherein the method further comprises the step of unblocking the drop plate prior to sliding the drop plate from the dispensing path into the release position.

35. The method according to claim 34, wherein the drop plate is manually unblocked.

36. The method according to claim 28, wherein the drop plate is retained directly to the tray in the drop direction.

37. The method according to claim 28, wherein the medicine dispensing device further comprises a frame for holding the tray, wherein the drop plate is retained directly to the frame.

* * * * *